United States Patent
Matsuda et al.

(10) Patent No.: US 6,768,545 B2
(45) Date of Patent: Jul. 27, 2004

(54) PARTICLE DETECTOR

(75) Inventors: Tomonobu Matsuda, Tokyo (JP); Takashi Minakami, Tokyo (JP)

(73) Assignee: Rion Co., Ltd., Tokyo (JP)

( * ) Notice: Subject to any disclaimer, the term of this patent is extended or adjusted under 35 U.S.C. 154(b) by 51 days.

(21) Appl. No.: 10/241,080

(22) Filed: Sep. 11, 2002

(65) Prior Publication Data

US 2003/0223062 A1 Dec. 4, 2003

(30) Foreign Application Priority Data

May 28, 2002 (JP) ........................................ 2002-153701

(51) Int. Cl.[7] .............................................. G01N 21/00
(52) U.S. Cl. ........................ 356/338; 356/339; 356/335; 356/336; 250/222.2
(58) Field of Search ................................ 356/339, 335, 356/336, 436; 250/222.2

(56) References Cited

U.S. PATENT DOCUMENTS

| | | | | |
|---|---|---|---|---|
| 5,642,193 A | * | 6/1997 | Girvin et al. ................ | 356/339 |
| 5,726,753 A | | 3/1998 | Sandberg | |
| 5,864,399 A | * | 1/1999 | Girvin et al. ................ | 356/339 |
| 5,903,307 A | * | 5/1999 | Hwang ..................... | 348/208.1 |
| 5,946,092 A | * | 8/1999 | DeFreez et al. ............. | 356/336 |
| 5,946,093 A | * | 8/1999 | DeFreez et al. ............. | 356/339 |
| 6,137,572 A | * | 10/2000 | DeFreez et al. ............. | 356/336 |

FOREIGN PATENT DOCUMENTS

JP  59-104533  6/1984

* cited by examiner

*Primary Examiner*—Frank G. Font
*Assistant Examiner*—Roy M. Punnoose
(74) *Attorney, Agent, or Firm*—Carrier, Blackman & Associates, P.C.; Joseph P. Carrier; William D. Blackman

(57) ABSTRACT

A particle detector comprising an optical cavity constructed of a solid-state laser which is optically pumped by pumping light generated from a pumping light source and a reflecting mirror, the optical cavity generating laser light, a flow path defined by sample fluid, and a particle detecting region where the laser light La is radiated upon the flow path, wherein particles passing through the particle detecting region are detected by receiving light scattered from the laser light due to the particles passing through the particle detecting region, and wherein the laser light generated within the optical cavity has a multi transverse mode, the cross sectional shape of which has a different length in the longitudinal direction and the transverse direction.

13 Claims, 2 Drawing Sheets

PARTICLE DETECTOR

BACKGROUND OF THE INVENTION

1. Field of the Invention

The present invention relates to a particle detector for detecting particles contained in fluid in which the fluid to be scanned is introduced into a particle detecting region defined by radiated laser light.

2. Description of the Prior Art

At a manufacturing site for precise electronic devices, higher decontamination has been required for areas such as a clean room. It is necessary to pass a great volume of sample fluid through a flow path of a particle detector at one time so as to detect particles in a highly decontaminated condition. Also, it is necessary to increase a cross-sectional area of a flow path so as to pass a great volume of sample fluid, and as a result of increasing a cross-sectional area of a flow path, it is necessary to expand a laser beam so as to secure a particle detecting region.

As disclosed in Japanese Unexamined Patent Application Publication No. Sho 59-104533, there has been already known a conventional particle detector in which a flow rate of a sample is increased by employing a multimode laser using a plasma tube.

However, the transverse mode pattern of such a multi-mode laser using a plasma tube, such as a He-Ne gas laser, has a circular shape because the plasma tube is comprised of a capillary glass tube having a circular cross section.

Accordingly, if a laser beam having a circular cross section is expanded, the energy density thereof is deteriorated, an amount of light scattered by particles is decreased, and thereby it becomes difficult to detect fine particles. Also, since the plasma tube is comprised of glass, it is inferior in the thermal and mechanical strength, optical axis displacement may occur, and there is a strong likelihood that the accuracy of detecting particles will be deteriorated. In addition, the particle detector is large-sized because of using a plasma tube, and thereby it is not user-friendly.

As a particle detector using a solid-state laser for miniaturization, there has been known a particle detector in which a laser beam has a single transverse mode such as disclosed in U.S. Pat. No. 5,726,753. However, it is impossible to expand such laser beam of a single mode.

In a conventional particle detector shown in FIG. 4, the beam thickness having a single mode (the beam diameter at the end surface of a solid-state laser 102) ω is obtained by the following equation (1):

$$\omega = 2\left(\left(\frac{\lambda}{\pi}\right)^2 L(R-L)\right)^{\frac{1}{4}} \quad \text{[Equation 1]}$$

In this equation, λ indicates the wavelength of laser light La within an optical cavity 100, L indicates the length of the optical cavity 100, and R indicates the radius of curvature of a reflecting mirror 101. Also, the reference numeral 103 refers to a semiconductor laser which functions as a light source for optical pumping, and the reference numeral 104 refers to a condenser lens. FIG. 5 is a graph showing the intensity distribution of a laser beam in a single mode.

As is apparent from Equation 1, for a practical optical cavity length, it is difficult to achieve a beam diameter of 1 mm or more. Therefore, if a great volume of sample fluid (for example, 28.3 liter/min.) is to be passed through, it is necessary to increase the flow velocity. As a result, light interference occurs due to the flow of the sample fluid, which causes a noise increase, and thereby it is difficult to detect fine particles.

It is therefore an object of the present invention to provide a particle detector which allows a great volume of sample fluid to pass through a flow path at one time and thereby achieve accurate monitoring in high decontamination conditions.

SUMMARY OF THE INVENTION

For solving the above-mentioned problems, according to the present invention, there is provided a particle detector comprising an optical cavity constructed of a solid-state laser which is optically pumped by pumping light generated from a pumping light source and a reflecting mirror, the optical cavity generating laser light, a flow path defined by sample fluid, and a particle detecting region where the laser light is radiated upon the flow path, wherein particles passing through the particle detecting region are detected by receiving light scattered from the laser light due to the particles passing through the particle detecting region, and wherein the laser light generated within the optical cavity has a multi transverse mode.

According to another aspect of the present invention, the cross sectional shape of the laser light has a different length in the longitudinal direction and the transverse direction.

DETAILED DESCRIPTION OF THE PREFERRED EMBODIMENTS

Preferred embodiments of the present invention will now be described with reference to the accompanying drawings.

Figure 1:
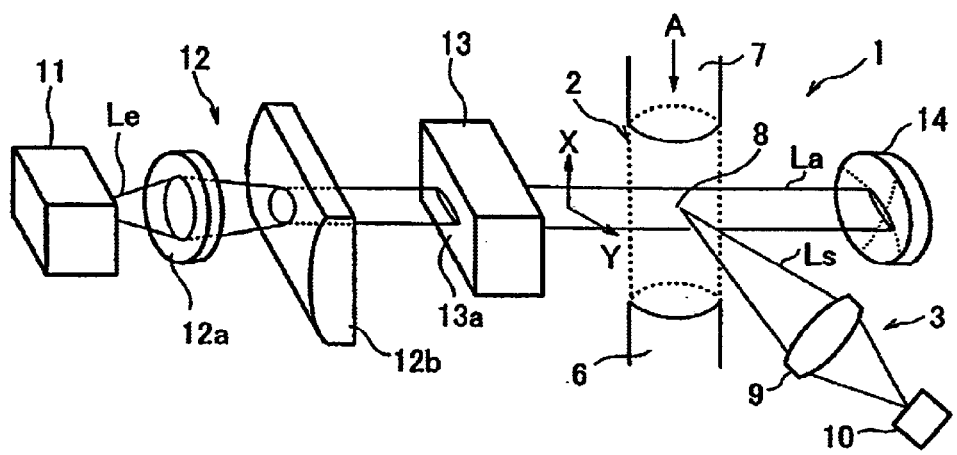
FIG. 1 shows a schematic structure of the first embodiment of a particle detector according to the present invention.

The first embodiment of a particle detector according to the present invention, as shown in FIG. 1, is comprised of an optical cavity 1 for generating laser light La, a flow path 2 which is defined by fluid to be scanned, and a light receiving portion 3 for receiving scattered light Ls.

The optical cavity 1 is comprised of a semiconductor laser 11 for generating pumping laser light Le, a condenser lens system 12 for condensing the pumping laser light Le, a solid-state laser 13 which receives the condensed pumping laser light Le and thereby emits laser light La through optical pumping, and a concave mirror 14 for reflecting the laser light La from the solid-state laser 13 back to the solid-state laser 13, the concave mirror 14 being provided to be opposed to the solid-state laser 13 in which the flow path 2 is provided therebetween.

The condenser lens system 12 is comprised of a convex lens 12a having a spherical shape and a cylindrical lens 12b. The pumping laser light Le is condensed by the convex lens 12a and thereafter converted into an elongated shape with respect to the transverse mode pattern by the cylindrical lens 12b.

The pumping laser light Le having an elongated transverse mode pattern refers to a condition where the cross section of the laser beam has an elongated shape, specifically the laser beam is made to be short in the direction of the flow path 2 (hereinafter referred to as an X-direction) and long in the direction perpendicular to the flow path 2 (hereinafter referred to as a Y-direction), and more specifically the laser beam is flattened to be long in the transverse direction (Y-direction) over the thickness ω of the beam having a single transverse mode obtained by equation (1).

As the solid-state laser 13, for example, Nd:YVO$_4$, Nd:YAG, or the like can be used. At the end surface of the solid-state laser 13 facing toward the condenser lens system 12 are formed an antireflection coating through which the pumping wavelength of the semiconductor laser 11 (the optical pumping wavelength of the solid-state laser 13) can penetrate and a reflection coating which reflects the oscillating wavelength of the solid-state laser 13. At the end surface of the solid-state laser 13 facing toward the concave mirror 14 is formed an antireflection coating that is antireflective with respect to the oscillating wavelength of the solid-state laser 13.

Figure 3:
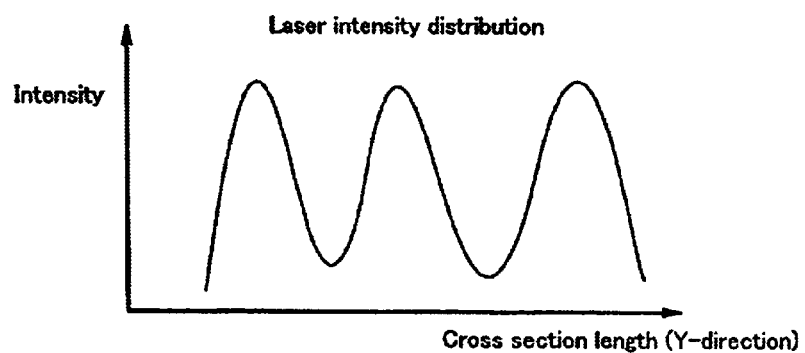
FIG. 3 is a graph showing the intensity distribution of a laser beam in a multi mode.
Figure 4:
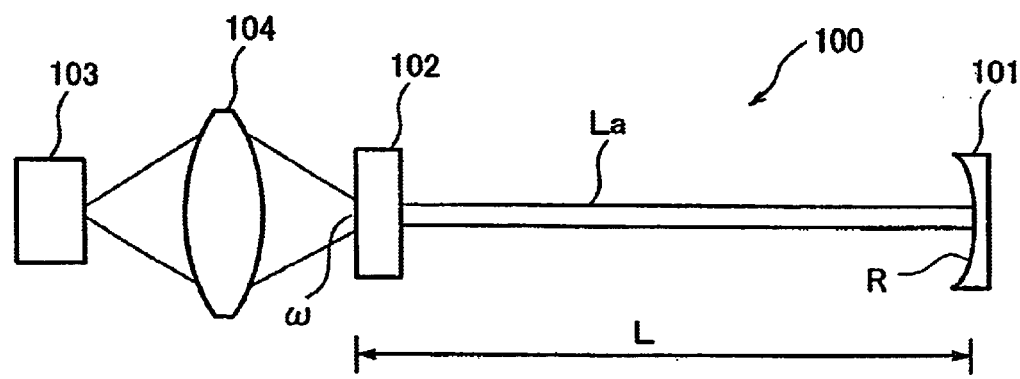
FIG. 4 shows a schematic structure of a conventional particle detector using a single mode.
Figure 5:
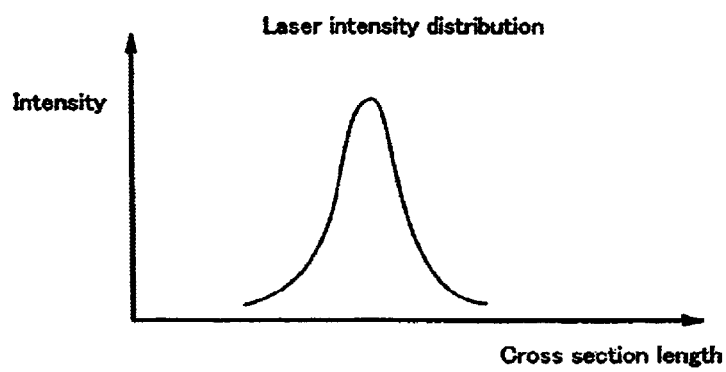
FIG. 5 is a graph showing the intensity distribution of a laser beam in a single mode.

The solid-state laser 13 emits laser light La having an elongated (flattened) transverse mode pattern in the direction perpendicular to the optical axis and having a multimode with respect to the transverse direction (multi transverse mode) from the end surface thereof. The laser light La having a multi transverse mode refers to laser light of an intensity distribution having a plurality of (for example, three) peak values in the Y-direction of the beam cross section such as shown in FIG. 3.

The concave mirror 14 has a reflecting surface having a concave shape, the radius of curvature of which is smaller in the X-direction than in the Y-direction. On the reflecting surface, a reflecting coating for reflecting the laser light La is applied. The optical axis of the concave mirror 14 is perpendicular to a surface 13a on which the reflection coating which reflects the oscillating wavelength of the solid-state laser 13 is applied.

The laser light La generated within the optical cavity 1, that is, the laser light La resonating between the solid-state laser 13 and the concave mirror 14 is kept in a multi transverse mode state.

The flow path 2 is defined by fluid to be scanned flowing from an inlet 7 to an outlet 6 in a direction shown by an arrow A in the drawing, the fluid being aspirated by an aspirating pump (not shown in the drawing) connected with the downstream portion of the outlet 6. The portion where the laser light La and the flow path 2 intersect is a particle detecting region 8.

Also, by selecting the cylindrical lens 12b, it is possible to make the width of the laser light La in the Y-direction and the width of the flow path 2 coincide with each other. When the width of the laser light La in the Y-direction and the width of the flow path 2 coincide with each other, the whole cross section of the flow path 2 can be the particle detecting region 8 and thereby all particles passing through the flow path 2 can be detected. For example, if the cross section of the flow path 2 has a circular shape, it is possible to make the width of the laser light La in the Y-direction coincide with the diameter of the flow path 2.

The light receiving portion 3 is comprised of a condenser lens 9 for condensing scattered light Ls which is generated at the particle detecting region 8 and a photodiode 10 for photoelectrically converting the condensed scattered light Ls. The light receiving portion 3 receives scattered light Ls which is generated by radiating the laser light La onto particles at the particle detecting region 8 in a case where the fluid contains particles, and outputs electrical signals depending on the intensity of the scattered light Ls.

In the first embodiment of a particle detector according to the present invention having the above-mentioned structure, by allowing the laser light La generated within the optical cavity 1 to have a multi transverse mode pattern, widening the laser light La in the direction perpendicular to the flow path 2 (Y-direction) and narrowing the laser light La in the direction parallel to the flow path 2 (X-direction), it is possible to improve the energy density and expand the cross section of the beam perpendicular to the flow path 2.

Also, by reducing the thickness in the X-direction, it is possible to control the increase in the volume of the particle detecting region, and thereby the increase of background light due to air molecules can be controlled and the increase of noise can also be controlled.

In addition, when the width of the laser light La in the Y-direction and the width of the flow path 2 coincide with each other, the whole cross section of the flow path 2 can be the particle detecting region 8 and thereby all particles passing through the flow path 2 can be detected.

Consequently, by allowing the laser light La to have a multi transverse mode pattern and expanding the cross section of the beam, it is possible to increase the cross-sectional area of the flow path 2 and flow a great volume of sample fluid through the flow path 2 at one time. As a result of this, it is possible to achieve a particle detector which enables accurate monitoring in high decontamination conditions.

Also, by using a solid-state laser instead of a conventional plasma tube, it is possible to achieve a downsized optical cavity having a simple structure and manufacture a particle detector having superior mechanical strength.

Figure 2:
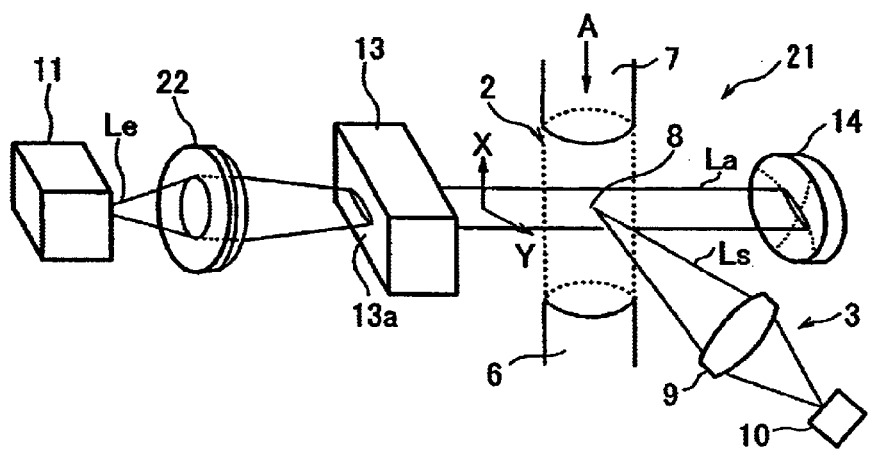
FIG. 2 shows a schematic structure of the second embodiment of a particle detector according to the present invention.

Next, the second embodiment of a particle detector according to the present invention, as shown in FIG. 2, is comprised of an optical cavity 21 for generating laser light La, a flow path 2 which is defined by fluid to be scanned, and a light receiving portion 3 for receiving scattered light Ls.

The optical cavity 21 is comprised of a semiconductor laser 11 for generating pumping laser light Le, a spherical lens 22 for condensing the pumping laser light Le, a solid-state laser 13 which receives the condensed pumping laser light Le and thereby emits laser light La through optical pumping, and a concave mirror 14 for reflecting the laser light La from the solid-state laser 13 back to the solid-state laser 13, the concave mirror 14 being provided to be opposed to the solid-state laser 13 in which the flow path 2 is provided therebetween. The explanation of the elements having the same reference numerals as in FIG. 1 will be omitted.

The spherical lens 22 is a convex lens having a spherical shape. The focal length of the spherical lens 22 is adjusted so as to satisfy the conditions that the beam shape of the pumping laser light Le directed to the solid-state laser 13 is flattened and the laser light La radiated from the solid-state laser 13 has a multi transverse mode.

In the second embodiment of a particle detector according to the present invention having the above-mentioned structure, since there is an astigmatic difference in the pumping laser light Le generated from the semiconductor laser 11, the beam shape condensed by the spherical lens 22 becomes flat or nearly circular depending on the distance from the semiconductor laser 11.

Therefore, by adjusting the focal length of the spherical lens 22, it is possible to satisfy the conditions that the beam shape of the pumping laser light Le directed to the solid-state laser 13 is flattened and the laser light La radiated from the solid-state laser 13 has a multi transverse mode. As a result of this, it is possible to obtain the laser light La having a high energy density and having a multi transverse mode in which the beam cross section in the direction perpendicular to the flow path 2 (Y-direction) is expanded.

Also, by allowing the laser light La to have a multi transverse mode and expanding the cross section of the beam, it is possible to increase the cross-sectional area of the flow path 2 and flow a great volume of sample fluid through the flow path 2 at one time. As a result of this, it is possible to achieve a particle detector which enables accurate monitoring in high decontamination conditions.

As described above, according to the present invention, by allowing the laser light generated within the optical cavity to have a multi transverse mode, it is possible to improve the energy density and expand the cross section of the beam perpendicular to the flow path. Consequently, it becomes easy to increase the cross-sectional area of the flow path and flow a great volume of sample fluid through the flow path at one time, and thereby it is possible to achieve a particle detector which enables accurate monitoring in high decontamination conditions.

Also, by using a solid-state laser, it is possible to achieve a downsized optical cavity having a simple structure and manufacture a particle detector having superior mechanical strength.

According to the present invention, by allowing the laser light generated within the optical cavity to have a multi transverse mode, widening the laser light in the direction perpendicular to the flow path and narrowing the laser light in the direction parallel to the flow path, it is possible to improve the energy density and expand the cross section of the beam perpendicular to the flow path. Consequently, it becomes easy to increase the cross-sectional area of the flow path and flow a great volume of sample fluid through the flow path at one time, and thereby it is possible to achieve a particle detector which enables accurate monitoring in high decontamination conditions.

Also, by reducing the laser light thickness, it is possible to control the increase in the volume of the particle detecting region, and thereby the increase of background light due to air molecules can be controlled and the increase of noise can also be controlled.

Although there have been described what are the present embodiments of the invention, it will be understood by persons skilled in the art that variations and modifications may be made thereto without departing from the gist, spirit or essence of the invention.

What is claimed is:

1. A particle detector comprising:
   an optical cavity constructed of a solid-state laser which is optically pumped by pumping light generated from a pumping light source and a reflecting mirror, said optical cavity generating laser light;
   a flow path defined by sample fluid; and
   a particle detecting region where said laser light is radiated upon said flow path,
   wherein particles passing through said particle detecting region are detected by receiving light scattered from said laser light due to said particles passing through said particle detecting region, and wherein said laser light generated within said optical cavity has a multi transverse mode.

2. The particle detector according to claim 1, wherein a cross sectional shape of said laser light has a different length in the longitudinal direction and the transverse direction.

3. The particle detector according to claim 2, wherein the transverse length of the cross sectional shape of said laser light is longer than the longitudinal length of the cross sectional shape of said laser light.

4. The particle detector according to claim 3, wherein the transverse length of the cross sectional shape of said laser light is equal to a diameter of said sample fluid flow path.

5. The particle detector according to claim 4, wherein said sample fluid flow path is substantially circular in cross section.

6. The particle detector according to claim 1, further including a light receiving portion which receives said scattered light.

7. The particle detector according to claim 1, further including a condenser lens system which converts said pumping light from the pumping light source into an elongated shape with respect to a transverse mode pattern before said pumping light passes through said solid state laser.

8. The particle detector according to claim 7, wherein said condenser lens system comprises a convex lens and a cylindrical lens.

9. The particle detector according to claim 7, wherein said condenser lens system comprises a convex lens.

10. The particle detector according to claim 9, wherein a focal length of said spherical convex lens is adjusted such that the laser light emitted from said solid state lens has said multi transverse mode.

11. The particle detector according to claim 1, wherein a transverse width of said laser light is equal to a diameter of said sample fluid flow path.

12. The particle detector according to claim 11, wherein said transverse width of said laser light is larger than a height of said laser light in a direction of said sample fluid flow path.

13. The particle detector according to claim 12, wherein said sample fluid flow path is substantially circular in cross section.

* * * * *

UNITED STATES PATENT AND TRADEMARK OFFICE
CERTIFICATE OF CORRECTION

PATENT NO. : 6,768,545 B2
DATED : July 27, 2004
INVENTOR(S) : Matsuda et al.

Page 1 of 1

It is certified that error appears in the above-identified patent and that said Letters Patent is hereby corrected as shown below:

<u>Column 1,</u>
Line 10, in the heading, between "of the" and "Art" change "Prior" to -- Relevant --.

Signed and Sealed this

Eighteenth Day of January, 2005

JON W. DUDAS
*Director of the United States Patent and Trademark Office*